United States Patent
Palmer

(10) Patent No.: US 8,500,621 B2
(45) Date of Patent: Aug. 6, 2013

(54) METHOD FOR MAKING A BLOOD PUMP

(76) Inventor: Arthur Palmer, Chicago, IL (US)

( * ) Notice: Subject to any disclaimer, the term of this patent is extended or adjusted under 35 U.S.C. 154(b) by 246 days.

(21) Appl. No.: 12/846,405

(22) Filed: Jul. 29, 2010

(65) Prior Publication Data

US 2011/0009688 A1    Jan. 13, 2011

Related U.S. Application Data

(60) Division of application No. 11/788,668, filed on Apr. 20, 2007, now Pat. No. 7,803,105, which is a continuation-in-part of application No. PCT/US2005/038635, filed on Oct. 25, 2005.

(60) Provisional application No. 60/621,920, filed on Oct. 25, 2004.

(51) Int. Cl.
*A61M 1/10* (2006.01)

(52) U.S. Cl.
USPC .......................................................... 600/16

(58) Field of Classification Search
USPC ............................................ 600/16; 623/3.1
See application file for complete search history.

(56) References Cited

U.S. PATENT DOCUMENTS

| | | |
|---|---|---|
| 3,406,633 A | 10/1968 | Schomburg |
| 3,630,644 A | 12/1971 | Bellhouse et al. |
| 3,791,767 A | 2/1974 | Shill |
| 3,985,134 A | 10/1976 | Lissot et al. |
| 4,133,616 A | 1/1979 | Poirier |
| 4,222,127 A | 9/1980 | Donachy et al. |
| 4,231,366 A | 11/1980 | Schael |
| 4,376,312 A | 3/1983 | Robinson et al. |
| 4,552,552 A | 11/1985 | Polaschegg et al. |
| 4,557,673 A | 12/1985 | Chen et al. |

(Continued)

FOREIGN PATENT DOCUMENTS

| | | |
|---|---|---|
| CH | 0539203 | 7/1973 |
| EP | 0629412 | 12/1994 |

(Continued)

OTHER PUBLICATIONS

Avrahami, et al. "Hemodynamic Aspects of the Berlin Ventricular Assist Device" Department of Biomedical Engineering Tel Aviv University IEEE 2001.*

(Continued)

*Primary Examiner* — Carl H Layno
*Assistant Examiner* — Elizabeth K So
(74) *Attorney, Agent, or Firm* — Greer, Burns & Crain, Ltd.

(57) ABSTRACT

A method of making a blood pump comprises selecting a desired flow pattern in a pumping chamber defined by an extensible bladder wherein the flow pattern is based generally on blood flow in a natural heart, using an initial computer model of the desired flow pattern to determine the material composition and dynamic operation conditions of each portion of the bladder, designing a bladder and pump operating system, computer modeling the actual design, testing and refining the design, and constructing a prototype based thereon. The desired flow pattern includes guiding and directing the flow of blood through the pumping chamber by reason of the action of an expansile bladder on the blood flow. A continuous circular or spiral fluid path is obtained that more effectively washes all areas of the bladder including the inlet and discharge ports with blood to reduce thrombosis.

11 Claims, 3 Drawing Sheets

U.S. PATENT DOCUMENTS

| | | | |
|---|---|---|---|
| 4,668,459 | A | 5/1987 | Joh |
| 4,707,315 | A | 11/1987 | Joh et al. |
| 4,851,002 | A | 7/1989 | Slonina |
| 4,938,766 | A | 7/1990 | Jarvik |
| 5,222,980 | A | 6/1993 | Gealow |
| 5,324,464 | A | 6/1994 | Holfert et al. |
| 5,599,173 | A | 2/1997 | Chen et al. |
| 6,030,335 | A | 2/2000 | Franchi |
| 6,045,496 | A | 4/2000 | Pacella et al. |
| 6,464,476 | B2 | 10/2002 | Ross et al. |
| 6,579,223 | B2 | 6/2003 | Palmer |
| 6,592,623 | B1 | 7/2003 | Bowlin et al. |
| 2002/0175449 | A1 | 11/2002 | Chu et al. |
| 2003/0018457 | A1 | 1/2003 | Lett et al. |
| 2003/0168756 | A1 | 9/2003 | Balkus, Jr. et al. |
| 2003/0228350 | A1 | 12/2003 | Chu et al. |
| 2004/0076661 | A1 | 4/2004 | Chu et al. |
| 2004/0177750 | A1 | 9/2004 | Wiechers et al. |
| 2005/0113868 | A1 | 5/2005 | Devellian et al. |
| 2005/0186243 | A1 | 8/2005 | Hunter et al. |
| 2007/0197857 | A1 | 8/2007 | Palmer |

FOREIGN PATENT DOCUMENTS

| | | |
|---|---|---|
| FR | 1439014 | 4/1966 |
| GB | 2004331 | 3/1979 |
| JP | 53-2996 | 1/1978 |
| JP | 55-113459 | 9/1980 |
| JP | 57-156770 | 9/1982 |
| JP | 2-261465 | 10/1990 |

OTHER PUBLICATIONS

Enriquez-Remigio "Incompressible flows in elastic domains: and immersed boundary method approach" Elsevier Inc. available online Oct. 12, 2004.*

Huang et al. "A review on polymer nanofibers by electrospinning and thier applications in nanocomposites" Composites Science and Technology 63 (2003) 2223-2253.*

Pernice, et al. "Final Report: Symposium on Adaptive Methods for Partial Differential Equations" University of Utah, Salt Lake City, Utah, Dec. 8, 1998.*

Sugawara et al. "Aortic blood momentum—the more the better for the ejecting heart in vivo?" Cardiovascular Research 33 (1997) 433-446.*

Jung et al. "Two-dimensional simulations of valveless pumping using the immersed boundary method" SIAM Journal of Scientific Computing, 2001 Society of Industrial and Applied Mathematics. vol. 23 No. 1 pp. 19-45.*

Eugene D. Boland, et al, Electrospinning of Biopolymers (Natural or Synthetic) for Tissue Engineering Scaffolds, "Polymer Preprints," 2003, 44(2), 92.

Charles S. Peskin, The Immersed Boundary Method, Cambridge University Press, 2002, pp. 1-39.

Jack D. Lemmonn, et al, Computational Modeling of Left Heart Diastolic Function article (from Dialog search of May 22, 2006), "Journal of biomechanical engineering," 2000, vol. 122, No. 4, pp. 297-303.

Schmid et al., Cerebral & Systematic Embolization During Ventricular Support With the Novacor N00 Device, "1968 Publication by The Society of Thoracic Surgeons," Published by Elsevier Science, Inc.—pp. 1703-1710.

Thomas et al., Neurologic Complicatios of the Novacor Left Ventricular Assist Device, "1968 Publication by The Society of Thoracic Surgeons," Published by Elsevier Science, Inc.—pp. 1311-1315.

Kilner et al., Asymmetric Redirection of Flow Through the Heart, an article in "Letters to Nature," vol. 404, Apr. 13, 2000, pp. 759-761.

Argenziano et al., Left Venticular Assist Devices, "Management of End-Stage Heart Disease," Chapter 16, 1998, pp. 197-211.

Kung, Total Artificial Heart, "Management of End-Stage Heart Disease," 1998, Chapter 17, pp. 213-219.

Frazier, Axial Flow Pumps, "Management of End-Stage Heart Disease," 1998, Chapter 18, pp. 221-227.

Nitta et al, An electromagnetically driven univalved artificial heart, "Artificial Heart 2," Chapter 10, 1990, pp. 87-91.

Yamada et al., Development of artificial heart with left and right ventricles using a linear pulse motor, "Artificial Heart 3," Chapter 12, 1990, pp. 101-105.

Umezu et al., Preliminary Study—Optimization of spiral vortex blood pump, "Artificial Heart 3," Chapter 13, 1990, pp. 107-114.

Imachi et al., Development of an artificial heart actuator for a compliance chamberless blood pump, "Artificial Heart 3," 1990, pp. 137-142.

Yukihiko Nose, Toward a totally implantable artificial heart: Development status at Cleveland Clinic, "Artificial Heart 3," Chapter 18, 1990, pp. 147-164.

Nakamura et al., Motor-deiven computer-controlled implantable cardiac assist device—An optical encoder for feedback control, "Artificial Heart 3," Chapter 21, 1990, pp. 183-197.

Snyder et al., The Penn State Implantable Artificial Heart: Current Status, "Artificial Heart 3," Chapter 24, 1990, pp. 205-212.

Goo Min et al., Design of moving actuator total, "Artificial Heart 3," Chapter 27, 1990, pp. 229-233.

* cited by examiner

METHOD FOR MAKING A BLOOD PUMP

REFERENCE

This application is a division of application Ser. No. 11/788,668 now U.S. Pat. No. 7,803,105, filed Apr. 20, 2007, which is a continuation-in-part of International PCT Application No. PCT/US2005/038635, filed Oct. 25, 2005, designating the United States, and claiming priority from U.S. Provisional Patent Application Ser. No. 60/621,920 filed Oct. 25, 2004, which applications are hereby incorporated by reference.

TECHNICAL FIELD

The subject application relates generally to fluid pumps, and more particularly to blood pumps, cardiac assist devices, methods for making blood pumps and blood pumping methods.

BACKGROUND ART

The natural heart functions in a fashion similar to a positive displacement pump. Each of the two pumping chambers in the natural heart has two check valves (an inlet and an outlet valve). The walls of the natural heart are made of contractile muscle that provide the power to pump the blood. Each pumping cycle consists of a filling or diastolic phase of the pumping cycle and an ejection or systolic phase of the pumping cycle. During the filling phase, the muscle fibers making up the walls of the heart relax allowing the chamber they surround to fill with blood. During the ejection phase of the cycle the muscle making up the walls of the heart contracts ejecting a portion of the blood from the chamber. The muscle making up the walls of the heart does not all relax simultaneously during the filling phase and does not all contract simultaneously during the ejection phase of the heart's pumping cycle. Portions relax sequentially during the filing phase and they contract sequentially during the ejection phase in such a way to direct or "milk" the blood through the heart in flow that is generally laminar with controlled levels of shear and other parameters of flow.

Mechanical blood pumps have been developed for use as artificial hearts to replace or assist the natural heart. Present blood pumps fall into two general categories. One category uses a rotary impeller and includes centrifugal pumps and axial flow pumps. The other category is pulsatile pumps that provide a flow pattern that more resembles that of the natural heart. My earlier patent, U.S. Pat. No. 6,579,223, discloses a pump with desirable pulsatile flow. This pump comprises a housing, an extensible bladder within the housing, a driving fluid between the bladder and the housing, and a device such as a vacuum pump to cyclically decrease and increase the pressure of the driving fluid to expand and contract the elastic bladder. This pump is designed to milk the blood through the apparatus, by progressively expanding the bladder in the direction of fluid flow and progressively contracting the bladder, also in the direction of flow. The pumping chamber has an inlet and an outlet, each of which is equipped with a one-way flow check valve. The elastic expansion and contraction of the bladder reduces the formation of blood clots (thrombosis) in the pump.

A problem with some prior art blood pumps relates to the pattern of blood flow through the pump, i.e., the flow pattern. Significant turbulence occurs in the pumping chamber during the pumping cycle and fluid flow parameters such as shear may not remain in physiological range. There is little other than changing the dimensions and geometry of the pumping chamber that can be done to control the characteristics of blood flow through the pumping chamber. There are areas of high velocity with potential high shear and other areas of slow flow. The areas of high shear may activate platelets and the activated platelets will then contribute to clot formation in slow flow areas. Turbulence leads to energy loss and inefficiency of the pump. Excessive turbulence can also damage the blood cells. Although my prior patent addresses this issue, further improvements are needed in creating a flow pattern that resembles that of a natural heart. Also, there is a need for a process of designing the pump components, particularly the bladder, to achieve the desired flow pattern.

SUMMARY OF THE INVENTION

The present disclosure builds on my prior patent, U.S. Pat. No. 6,579,223, entitled Blood Pump. The object of the invention is to provide for improved flow through the pump, for harnessing the inertial forces of the pumped fluid and for improved blood flow through the pumping chamber to better control local fluid shear, turbulence and washing of the areas of the pump susceptible to thrombosis (clotting) thereby decreasing thrombosis in these susceptible areas. In addition a process is provided for the design and construction of the pump. Although this disclosure focuses primarily on pumping blood, it is contemplated that principles herein are applicable to other fluids.

Presently available diaphragm type pumps draw the fluid being pumped through an intake port into a pumping chamber. Aside from redesign of the geometry of the device, they have little or no ability to guide the flow of fluid through the pumping chamber. Once the pumping chamber has filled, the fluid in the chamber must slow or stop. In the ensuing ejection phase of the pumping cycle, the fluid is accelerated toward the discharge port, which in at least some pumps, is in a direction that is opposite the direction of the intake flow. Flow momentum is lost, and considerable turbulence is created. Although available designs may vary in construction and geometry, they generally function as just described.

One aspect of the present invention is to guide and direct the flow of blood through the pumping chamber by reason of the action of an expansile bladder on the blood flow. A continuous circular or spiral fluid path is obtained that more effectively washes the inlet and discharge ports as well as the walls of the pumping chamber with the pumped fluid, i.e., blood. Control of fluid shear and good washing of all areas of the bladder will decrease the tendency for blood clotting. The blood is initially drawn into the pumping chamber through the inlet port. As the blood flows into the pumping chamber it washes past the discharge port. As various areas of the bladder sequentially expand and contract, the blood is guided through the pumping chamber washing the chamber walls. Prior to being ejected out of the discharge port, the blood washes past the inlet port. It is expected that the flow of blood directed across the inlet and discharge ports and the washing action associated with this flow will decrease clotting in these areas. Also, by appropriately directing the flow of the blood through the device and optimizing the angle of the inlet and the discharge port, the inertia of the blood will contribute to the action of the bladder and the path of the blood flow through the device. A smoother laminar flow through the pumping chamber afforded by the expansible bladder will improve the efficiency of the pump and decrease energy requirements.

One of the important initiators of blood clotting is the platelet. Platelets are formed elements that are manufactured in the bone marrow and circulate in the bloodstream along with red cells, white cells and other formed elements. Platelets normally circulate in an inactivated state. There are many diverse stimuli that can activate platelets causing them to adhere to surfaces, to aggregate and initiate clotting. One of these stimuli is the level of shear. Areas of high shear may activate platelets then if the activated platelets flow through a region of low shear, or slow flow, they may begin to form a clot. Control of shear stress by controlling parameters of flow, such as local velocity is very important in artificial blood pumps. The embodiments of the present invention provide more control over local velocity than previously available designs.

A process for designing, constructing and operating the pump, especially the bladder, comprises essentially two parts. The first part is to select a desired flow pattern and using sophisticated mathematical modeling techniques work backwards, so to speak, to arrive at the bladder function necessary to achieve that flow pattern. The second part of the method is to design a bladder and pump operating system to achieve the desired bladder function, and then to use the same mathematical modeling techniques to predict the resulting flow pattern. The design may be refined by repeating the foregoing steps.

More specifically, in the first part of the method, an initial pumping chamber configuration is selected or created, preferably with a circular or spiral shaped pumping chamber. A desired flow pattern, streamlines and other characteristics of blood flow through the device is designed guided by blood flow in a natural heart. An initial computer model of flow pattern will be developed using the mathematical techniques such as computational fluid dynamics and immersed boundary methods. This rigorous mathematical approach will provide the information to design the device in such a way to achieve the desired flow patterns and flow parameters. The initial computer model will be used to determine the position of various points of the bladder, as a function of time, throughout the pumping cycle. To induce laminar flow along these streamlines it may also be helpful to modify the shape of the bladder and pumping chamber.

In the second part of the method, a pump including a bladder, housing and pump operating system are designed. The pump is designed to operate such that each point or element of the bladder will move substantially in accordance with the initial computer model. To achieve this functionality, the bladder and operating system for driving the bladder preferably will function similar to that of a natural heart. The various elements of the bladder wall will not all expand simultaneously (or at the same rate) during the filling phase and will not all contract simultaneously (or at the same rate) during the ejection phase of the pumping cycle. Portions of the bladders will expand sequentially during the filing phase and contract sequentially during the ejection phase in such a way to direct or "milk" the blood through the pumping chamber in a generally laminar flow pattern.

The physical characteristics that the bladder will require at each point will be determined from the initial computer model (thickness, elasticity, viscoelasticity, fatigue strength and others). Appropriate materials will be selected for the bladder. In order to achieve the required characteristics at each point on the bladder, the thickness and composition of the bladder may vary, polymers or other materials may need to be combined in various areas by layering, forming bands or struts, electrospinning or other means. Preferably, the bladder is formed with directional elastic properties in the bladder wall that simulate heart muscles. It is further contemplated that the bladder operating system, including housing surrounding the bladder and means for driving the bladder will be adapted as necessary to achieve the designed sequential expansion and contraction of the bladder.

The bladder and pump operating system design are then tested, preferably by generating a computer model of the apparatus and generating simulated fluid flow using the same mathematical techniques described above, but now in the sequence of having a given pump design and generating the flow pattern therefrom. Problems in bladder and operating system design may mandate reversion back to previous steps with further modification of the size or shape of the housing, or shape or composition of the bladder, or means for driving the bladder. More than one simultaneous flow pathway through the bladder may be required. A prototype will be constructed based on the computer model. This will be bench tested followed by animal and human testing. Further refinement of the shell and bladder design will be made following prototype testing to simulate flow in natural hearts, eliminate stagnation points, provide laminar flow, wash ports, conserve energy, and reduce the potential for thrombosis.

BEST MODE FOR CARRYING OUT THE INVENTION

Figure 1A:
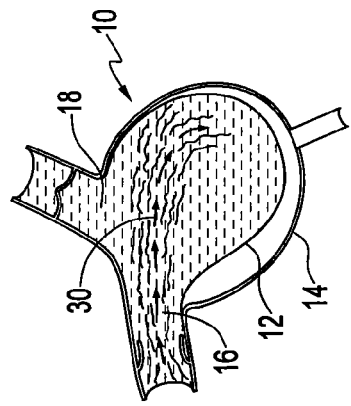
FIGS. 1A-1J diagrammatically illustrates a preferred method of pumping blood.
Figure 1B:
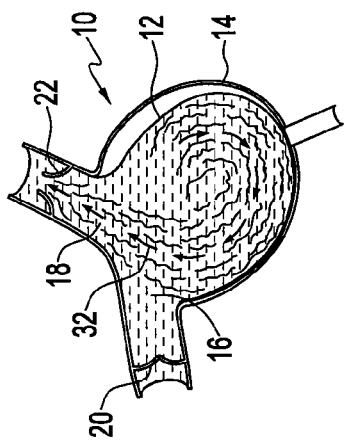
Figure 1C:
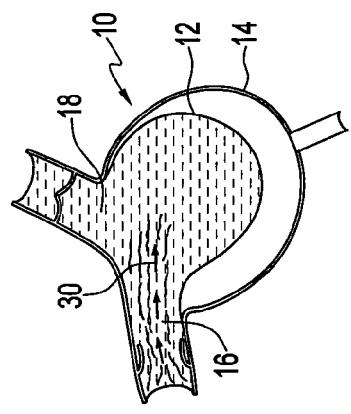
Figure 1D:
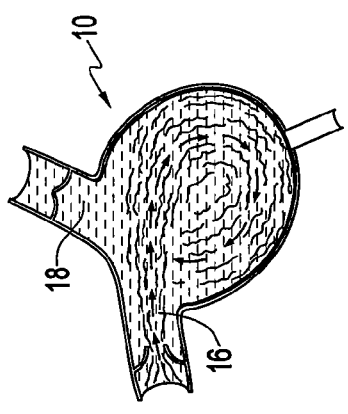
Figure 1E:
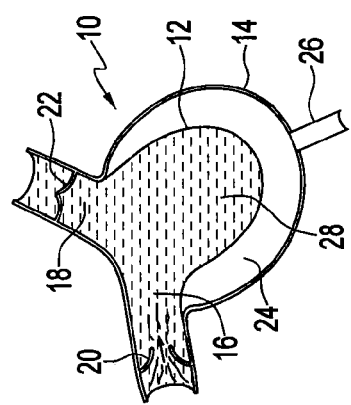
Figure 1F:
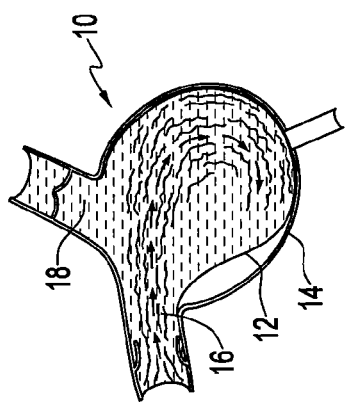
Figure 1G:
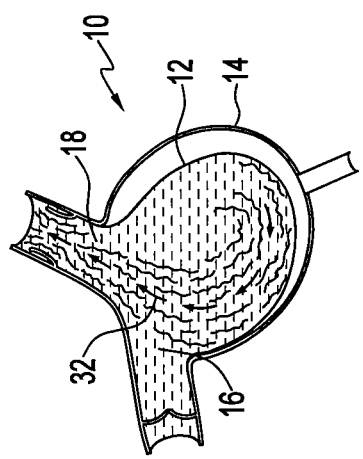
Figure 1H:
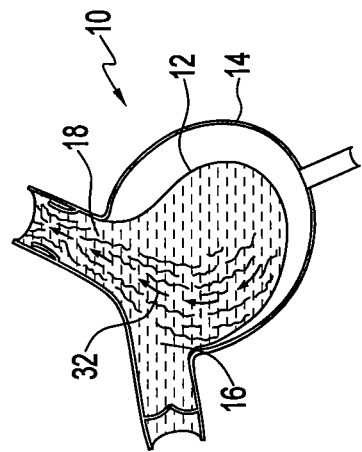
Figure 1I:
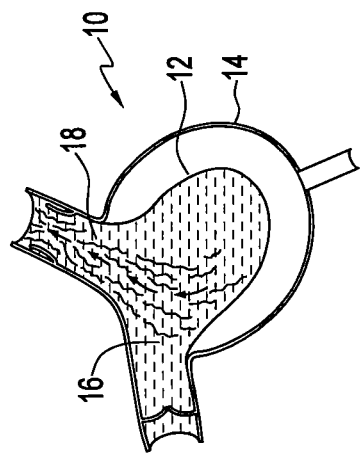

The following is a detailed description of certain embodiments of the invention presently deemed by the inventor to be the best mode of carrying out his invention. The invention as defined by the appended claims is not limited to these embodiments, and additional embodiments of the claimed inventive concept will undoubtedly be apparent to those skilled in the art.

Referring to the drawings, FIGS. 1A-1F illustrate a pump apparatus 10 constructed generally in accordance with my earlier patent, U.S. Pat. No. 6,579,223. Pump 10 comprises an expansile bladder 12 within a shell or housing 14. The bladder and housing in this embodiment are generally round for ease in illustrating the concept, and may be easier to begin with in the initial designs. Nevertheless, other shapes can be used and may be preferable, such as conical or heart-shaped bladders. The bladder has an inlet port 16 and a discharge port 18. The inlet and discharge ports are preferably adjacent to one another, but may be spaced apart. An inlet check valve 20 and an outlet check valve 22 insure one-way flow through the bladder. The bladder is connected to the shell or housing at the inlet and outlet. A volume or space 24 is defined between the bladder 12 and housing 14. A bladder driving fluid is adapted to be cyclically introduced into and removed from the space 24 through port 26. A pumping chamber 28 is defined within bladder 12. Various devices known in the art are commercially available for introducing and removing the driving fluid from the space 24, for example, a vacuum pump as described in U.S. Pat. No. 6,579,223. Further, pressure regulating means (omitted from the drawings for clarity) may be provided in the space 24 between the bladder and housing to regulate the pressure applied to various portions or segments of the bladder as a function of time during the pumping cycle, and thereby affect the desired sequence and rate of expansion and contraction of each segment of the elastic bladder. One example of a pressure regulating means is shown in FIG. 6 of U.S. Pat. No. 6,579,223 and others are known in the art. Still further, a driving means (not shown) may be utilized for mechanically or hydraulically driving selected portions of the bladder and assisting in controlling the direction, magnitude, rate and timing of movement of various portions of the bladder to achieve the designed dynamic bladder pumping cycle shown in FIGS. 1A-1J.

Figure 1J:
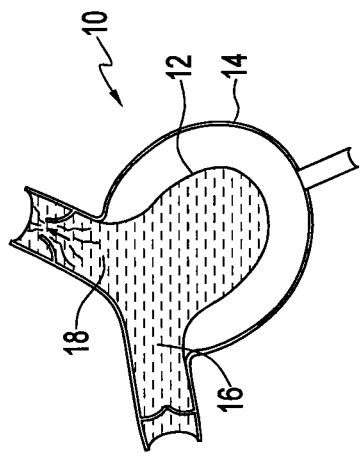

Preferably, the neutral or relaxed condition of the bladder is a fully contracted position, as shown in FIGS. 1A and 1J. By decreasing the pressure of the actuating fluid the bladder is elastically expanded to draw blood into the pumping chamber. By releasing the vacuum, the bladder retracts by reason of the elastic recoil of the bladder to eject blood from the pumping chamber. The ejection may also be augmented by positive pressure.

Referring now to FIGS. 1A through 1F, a method for pumping blood is diagrammatically illustrated wherein the blood is guided and directed through the pumping chamber by the expansile bladder. A fluid path through pump 10 more effectively washes the inlet 16 and discharge ports 18 and pumping chamber walls with the pumped fluid. The blood is initially drawn into the pumping chamber through the inlet port 16. FIG. 1A. As the blood flows into the pumping chamber through the inlet port, it washes past the discharge port, as shown by arrows 30 and flow lines in FIGS. 1B-1E. As various areas of the bladder 12 sequentially expand and contract, the blood is guided through the pumping chamber and washes past the inlet port 16 prior to being ejected out of the discharge port 18, as shown by arrows 32 and flow lines in FIGS. 1F-1I. It is expected that the flow of blood directed across the inlet and discharge ports and the washing action associated with this flow will decrease clotting in these areas. Also, by appropriately directing the flow of the blood through the device and optimizing the angle of the inlet and the discharge port, the inertia of the blood will contribute to the action of the bladder and the path of the blood flow through the device. The smoother laminar flow through the pumping chamber afforded by the expansible bladder will improve the efficiency of the pump and decrease energy requirements.

The specific configuration of pump 10 in FIG. 1 is merely to illustrate the pumping method, and should not be construed as limiting. For example, the housing or shell 14 of the pump is shown as generally cylindrical, but spiral, conical or other shapes may be used. Further, the particular means for expanding and contracting the bladder is not important as long as a smooth, laminar blood flow, guided and directed as explained above, is achieved.

Figure 2:
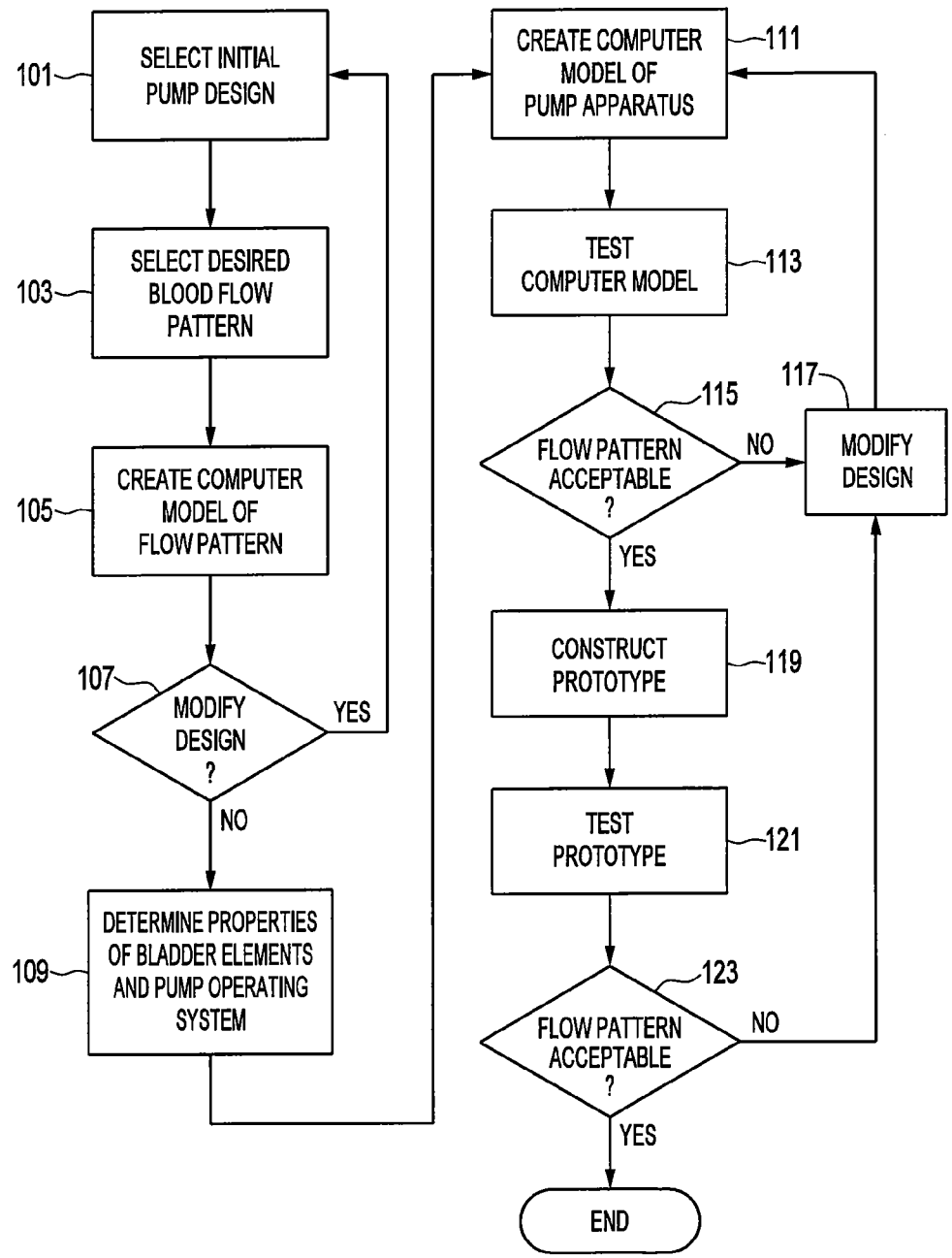
FIG. 2 is a flow diagram showing a preferred method for designing the pump.

A second aspect of the invention is a method for designing the bladder and pump operating system. It is an object of the invention to create a blood flow pattern similar to that of the natural heart, as described above. The design and composition of the bladder, housing and pump operating system are important factors in achieving the desired blood flow pattern. The bladder and operating system design process comprises a number of steps, which are shown in FIG. 2. The first step 101 is to select an initial housing and bladder shape, as shown for example in FIG. 1. Next, the desired streamlines and other characteristics of blood flow through the device, that is, the blood flow pattern, will be designed 103 based generally on blood flow in a natural heart.

A computer model of the blood flow pattern is developed 105. The computer model can be generated by any technique, for example by use of the mathematical techniques of computational fluid dynamics. Newer techniques, such as "Immersed Boundary Method" may be used. See, Peskin, Charles S., "The Immersed Boundary Method" *Acta Numerica* (2002) pp. 1-39. The Immersed Boundary Method is adaptable to computer simulation of the fluid-structure interaction. It is called for because in accordance herewith the size and shape of the pumping chamber is constantly changing throughout the pumping cycle, which in turn changes flow dynamics, which in turn affects bladder shape. A computer model will simulate the desired flow pattern. The computer model will be used to determine the position of various portions or elements of the bladder, as a function of time, throughout the pumping cycle. It may be necessary to refine or modify the initial design as shown at query 107, and repeat or revise steps 103, 105 and 107 until one is satisfied with the initial pump design and computer model.

The first part of the method thus uses a computer model in reverse, that is, the desired flow pattern is used to determine the structure, shape and function of the pump. The second part of the method uses information provided by the first part to design a prototype bladder and pump operating system, and then utilizes a computer model to predict the flow pattern in the prototype.

The initial computer model is used to determine the physical characteristics (e.g., thickness, elasticity, viscoelasticity, fatigue strength) of each element of the bladder wall 109 required for the given flow pattern. Appropriate materials will be selected for each element or portion of the bladder. In order to achieve the required characteristics of each element of the bladder, the thickness and material composition of the bladder may vary. Polymers or other materials can be combined in various areas by layering, forming bands or struts (as described in U.S. Pat. No. 6,579,223), electrospinning or other means. Electrospinning techniques, for example, may be used to design a continuous, unitary elastic bladder comprised of composite materials, where the composition and physical, viscoelastic and dynamic properties of the bladder vary from point to point in accordance with the computer model. See e.g., Boland, Eugene D. et al, "Electrospinning of Biopolymers (Natural and Synthetic) for Tissue Engineering Scaffolds" *Polymer Preprints* 2003, 44(2) at pp. 92-93; and U.S. patent publication No. 2003/0168756. Electrospinning techniques can be used to create directional elastic properties in the bladder that mimic the architecture and function of heart muscles. Indeed, it is preferred to simulate multiple muscle layers.

The pump operating system is designed, in cooperation with the bladder, to control the direction, magnitude, rate and timing of movement of each of the various portions of the bladder to achieve the designed dynamic bladder pumping cycle. More specifically, based on the computer model, the operating system causes portions of the bladder to expand sequentially during the filling phase and contract sequentially during the ejection phase in such a way to direct or "milk" the blood through the pumping chamber. The pump operating system includes a negative pressure device, such as a vacuum pump, for introducing and removing the driving fluid from the space 24 between the bladder and housing, and may optionally include pressure regulating means for regulating the pressure applied to various portions or segments of the bladder as a function of time during the pumping cycle, and/or a driving means for mechanically or hydraulically assisting in controlling the direction, magnitude, rate and timing of movement of various portions of the bladder to achieve the designed dynamic bladder pumping cycle. The particular devices utilized are within the skill of this highly specialized art, and are unimportant to the present invention as long as they substantially achieve the object of providing the desired movement of the bladder wall, which in turn provides the desired blood flow pattern.

The bladder and pump operating system are then tested 113, preferably by generating a computer model of the apparatus and generating simulated fluid flow 111. The flow pattern of the model is examined 115 to determine whether the design criteria are being met, including whether the flow is laminar, whether inertia of the blood is maintained, whether the discharge port is effectively washed by incoming flow, whether the exit port is washed by flow being ejected from the pump, whether areas of flow stagnation are avoided, whether zones of turbulent flow are avoided. Problems in bladder design may mandate reversion back to previous steps with further modification 117 of the size or shape of the housing, or shape or composition of the bladder, or design of the pump operating system. During this phase, progression from a two-dimensional to a three-dimensional model will occur. The design 117, computer modeling 111, testing 113 and evaluation 115 steps are modified or repeated until an acceptable flow pattern is achieved.

A prototype will then be constructed 119 based on the computer model. The prototype will be bench tested followed by animal and human testing 121. Test results will be evaluated 123. Further refinement of the bladder pump operating system 117 will be made following prototype testing to simulate flow in natural hearts, eliminate stagnation points, provide laminar flow, wash ports, conserve energy, and reduce the potential for thrombosis. The forgoing steps of computer modeling 111, testing 113 and evaluation 115, and prototype refinement 119, testing 121 and evaluation 123 are repeated as necessary to achieve the desired flow characteristics.

While preferred embodiments of the present invention have been shown and described, it is to be understood that these represent the best mode of practicing the invention contemplated by the inventor at the present time, and that various modifications and changes could be made thereto without departing from the scope of the invention as defined in the appended claims.

What is claimed is:

1. A method of providing a pump for pumping a fluid, comprising
    designing a desired initial fluid flow pattern in an extensible bladder having an elastic bladder wall and inlet and discharge ports,
    developing an initial mathematical computer model of the desired initial fluid flow pattern in the extensible bladder,
    determining the location, using the initial computer model of the desired initial fluid flow pattern, of various portions of the elastic bladder wall as a function of time that are required to induce the desired initial fluid flow pattern, wherein said determining the location considers an effect of movement of the elastic bladder wall on flow dynamics in the extensible bladder, and an effect of flow dynamics on a configuration of the bladder,
    determining physical characteristics of each portion of the elastic bladder wall and of a pump operating system such that viscoelastic properties vary throughout the bladder, and such that each portion of the bladder when elastically expanded and contracted will have movement as a function of time similar to the initial computer model and hence will approximate the desired initial fluid flow pattern, and thereafter
    computer modeling the pump with the elastic bladder and the pump operating system having a design that will elastically expand the bladder during a filling stage and the bladder elastically contracting in a discharge stage to generate a flow pattern approximating the desired initial fluid flow pattern, and thereafter
    constructing the pump including the bladder and the pump operating system based on the computer modeled pump.

2. A method of providing a pump as in claim 1, wherein the step of determining physical characteristics of each portion of the bladder includes selecting materials for each portion of the bladder and designing a continuous, unitary elastic bladder comprised of composite materials wherein the physical and viscoelastic properties of the bladder vary from portion to portion.

3. A method of providing a pump as in claim 1, further comprising the steps of
    simulating fluid flow in the computer modeled pump and modifying the bladder design or pump operating system design to more closely approximate the desired initial fluid flow pattern.

4. A method of providing a pump as in claim 1, wherein the fluid is blood, the inlet port to the bladder is adjacent to the discharge port, and the initial blood flow pattern includes directing blood flow from the inlet port to wash across and past the discharge port, directing the blood flow through the pumping chamber in a generally continuous curvilinear pattern, and directing the blood flow to wash across and past the inlet port as it is being ejected out the discharge port.

5. A method of providing a pump as in claim 1, wherein the fluid is blood and the initial blood flow pattern in the pumping chamber is substantially continuous maintaining the inertia of the blood flow, is essentially laminar, and is substantially free of stagnant and turbulent zones.

6. A method of providing a pump as in claim 1 wherein at least the initial computer modeling step utilizes the Immersed Boundary Method of computational fluid dynamics.

7. A method of providing a pump as in claim 1 wherein the bladder is comprised of plural material layers with directional elastic properties that mimic heart muscle layers.

8. A method of providing a pump as in claim 1, further comprising the step of
    determining if a flow pattern of the constructed pump is acceptable based on the desired initial fluid flow pattern, and
    if the determined flow pattern is not acceptable, modifying the design of the computer modeled pump.

9. A method of making a blood pump, comprising
    selecting an initial pump housing and bladder configuration,
    selecting an initial blood flow pattern for the pump based generally on blood flow in a natural heart,
    initial mathematical computer modeling the initial blood flow pattern,
    from the initial computer model, determining the location of various portions of the bladder as a function of time during the pumping cycle, wherein said determining the location considers an effect of movement of an elastic bladder wall on flow dynamics in the bladder, and an effect of flow dynamics on bladder configuration,
    from the initial computer model, determining the physical characteristics of each portion of the bladder,
    designing an elastic composite bladder comprised of selected materials for each bladder portion substantially meeting the physical characteristics for each respective portion, such that viscoelastic properties vary throughout the elastic composite bladder,
    designing a pump operating system such that the composite bladder and pump operating system will operate to control the direction, magnitude and timing of movement of each of the bladder portions to substantially replicate the location and movement of various portions of the bladder as a function of time during the pumping cycle as determined from the initial computer model, second mathematical computer modeling the elastic composite bladder and pump operating system,
simulating fluid flow in the elastic composite bladder and pump operating system with the second computer model, and
constructing a prototype blood pump based on the second computer model.

10. The method of claim 9 wherein at least the second computer modeling step utilizes the Immersed Boundary Method of computational fluid dynamics.

11. The method of claim 9 wherein the constructing step involves the use of electrospinning techniques in constructing the bladder, wherein the physical and viscoelastic properties of the constructed bladder vary from portion to portion.

* * * * *